US009003319B2

(12) United States Patent (10) Patent No.: US 9,003,319 B2
Linthicum et al. (45) Date of Patent: Apr. 7, 2015

(54) METHOD AND APPARATUS FOR DYNAMIC MULTIRESOLUTION CLINICAL DATA DISPLAY

(75) Inventors: Steven Linthicum, Lake In the Hills, IL (US); Steven Fors, Chicago, IL (US); Anthony Ricamato, West Chicago, IL (US); Eric Jester, Hoffman Estates, IL (US); Michael Mercado, Carol Stream, IL (US)

(73) Assignee: General Electric Company, Schenectady, NY (US)

( * ) Notice: Subject to any disclaimer, the term of this patent is extended or adjusted under 35 U.S.C. 154(b) by 1041 days.

(21) Appl. No.: 12/324,527

(22) Filed: Nov. 26, 2008

(65) Prior Publication Data

US 2010/0131883 A1 May 27, 2010

(51) Int. Cl.
*G06F 3/048* (2013.01)
*G06F 19/00* (2011.01)
(52) U.S. Cl.
CPC .......... *G06F 19/3406* (2013.01); *G06F 19/322* (2013.01)
(58) Field of Classification Search
USPC ....................................................... 715/771
See application file for complete search history.

(56) References Cited

U.S. PATENT DOCUMENTS

| | | | | |
|---|---|---|---|---|
| 2002/0109735 | A1* | 8/2002 | Chang et al. .................. | 345/853 |
| 2003/0233257 | A1* | 12/2003 | Matian et al. .................... | 705/3 |
| 2005/0125256 | A1* | 6/2005 | Schoenberg et al. ............. | 705/2 |
| 2008/0165140 | A1* | 7/2008 | Christie et al. ................ | 345/173 |
| 2009/0222286 | A1* | 9/2009 | Elsholz ............................ | 705/3 |

* cited by examiner

*Primary Examiner* — Peiyong Weng

(57) ABSTRACT

A multi-level information display system graphically represents clinical information for a user. The system includes a user interface providing clinical content to a user and accepting user input with respect to clinical content. The system also includes a graphical summary representation of a patient-related clinical data value. The graphical summary representation has one or more visible characteristics indicating an importance of the patient-related clinical data value. The system also includes a thumbnail trend view providing a graph of data elements used to provide the patient-related clinical data value shown in the graphical summary representation. The system further includes an originating data view retrieving and displaying, via the user interface, a source document corresponding to at least one data element on the graph shown in the thumbnail trend view. The various views are displayed via the user interface based on user manipulation of a cursor with respect to the displayed views.

15 Claims, 10 Drawing Sheets

FIG. 2

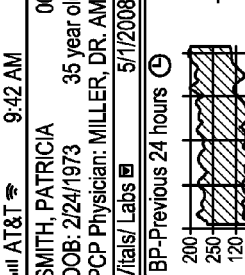

SMITH, PATRICIA  000111222  410
DOB: 2/24/1973  35 years old  Sex: Female  Referring Physician: MILLER, DR. AMANDA

Vitals/Labs — 5/1/2008  1:22 AM — 417

- Blood Pressure  200/130  ×
- Urinalysis  2+  ×
- 415
- Weight  197  ×
- Glucose  Negative  ×
- Temp  98.6  ×
- Allergies  None  ×

Clinical Details — 420 — 480

ADD-ON URINALYSIS
COLOR                   YELLOW
APPEARANCE              HAZY
SPECIFIC GRAVITY 425    1.011
PH                      6.5
PROTEIN (ACID PPT)      2+
GLUCOSE STRIP           NEGATIVE
KETONES         427     NEGATIVE
BILIRUBIN               NEGATIVE
OCCULT BLOOD            2+
WBC/HPF                 NONE OBSERVED
RBC/HPF                 NONE OBSERVED
CASTS/LPF               NONE OBSERVED
CRYSTALS/HPF            NONE OBSERVED
450  EPITH CELLS/HPF

Enter Search Criteria | Search — 460

Reason for Visit
- PRE-ECLAMPSIA
- SEVERE HEADACHE
- FACIAL SWELLING
470

Medications
- Hydralazine  100 mg QID  IV
- Tylenol  1000 mg BID  Oral

Radiology Studies
- Head CT  4/12/08
- Fetal US  4/05/08
430

Cardiology Studies
- ECG  4/12/08
- ECG  4/05/08
- ECG  3/29/08
440

Documents
▽ Progress Notes  Visit Date/Time

Documents
△ Progress Notes  Visit Date/Time
△ Progress Notes  Visit Date/Time
455

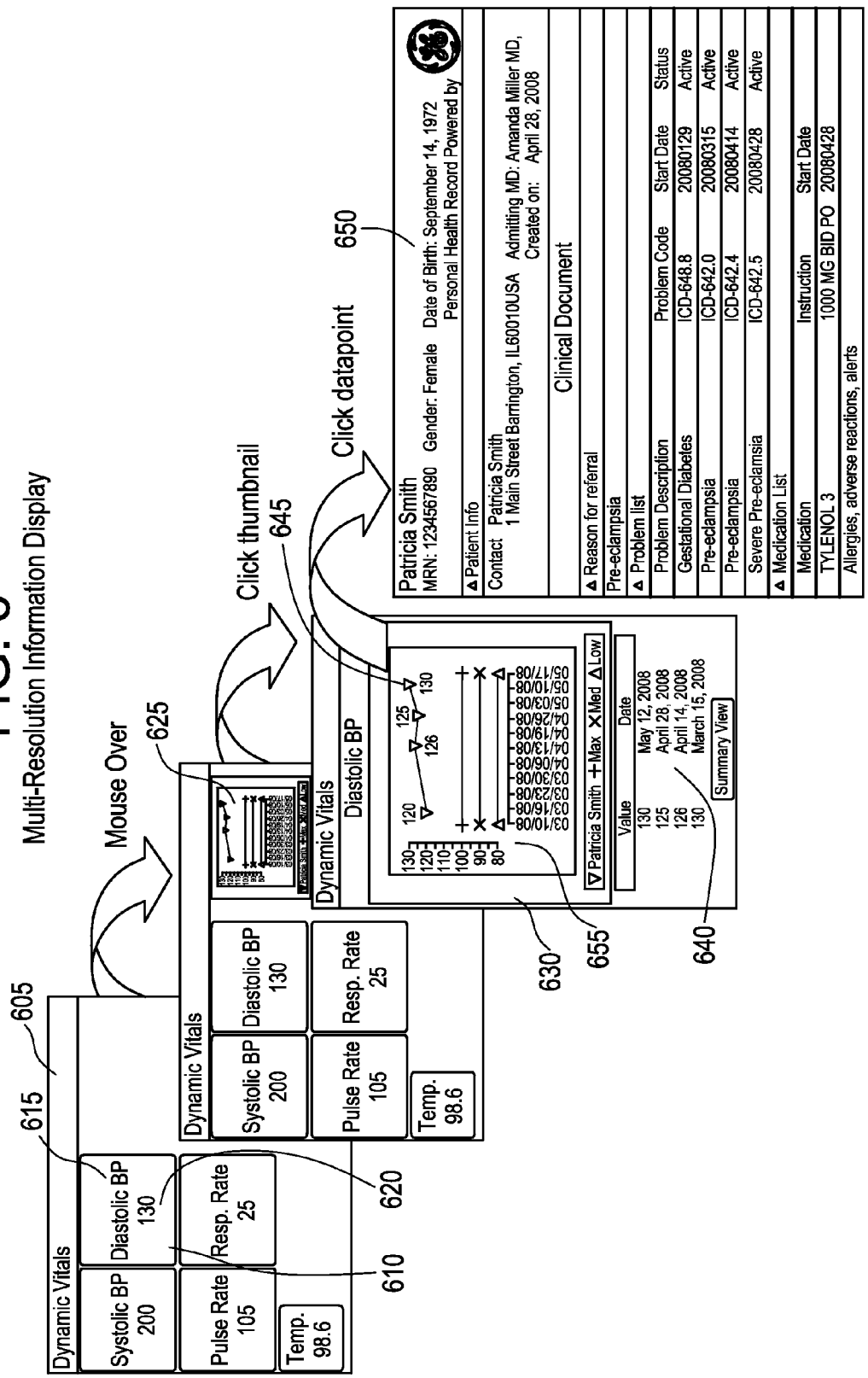

METHOD AND APPARATUS FOR DYNAMIC MULTIRESOLUTION CLINICAL DATA DISPLAY

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Current PACS and/or other reviewing systems provide all available medical information on a screen for a user. However, this information is not organized. In addition, there is currently no way to tell the user which of these data elements are important and which are not. Simply browsing through data is quite problematic as it is a huge disruption in a physician's workflow and often fails to yield the desired end user results.

A variety of clinical data and medical documentation is available throughout various clinical information systems, but it is currently difficult to find, organize, and effectively present the information to physicians and other healthcare providers at a point of care. There are a myriad of difficulties associated with this task. Current systems and methods perform static queries on single data sources, which generally returns information which may or may not be relevant and is typically incomplete.

Based on recent studies, computerized physician order entry errors have increased in approximately the last five years. According to the Journal of the American Medical Informatics Association in 2006, unintended adverse consequences from computer entry errors fell into nine major categories (in order of decreasing frequency): 1) more/new work for clinicians, 2) unfavorable workflow issues, 3) never-ending system demands, 4) problems related to paper persistence, 5) untoward changes in communication patterns and practices, 6) negative emotions, 7) generation of new kinds of errors, 8) unexpected changes in the power structure, and 9) and overdependence on technology. Poor usability and user interface design contributes to most if not all of these categories.

BRIEF SUMMARY OF THE INVENTION

Certain embodiments of the present invention provide systems and methods for providing adaptive, work-centered healthcare services via an adaptive user interface.

Certain embodiments provide a multi-level information display system graphically representing clinical information for a user. The system includes a user interface providing clinical content to a user and accepting user input with respect to clinical content. The system also includes a graphical summary representation of a patient-related clinical data value. The graphical summary representation has one or more visible characteristics indicating an importance of the patient-related clinical data value. The graphical summary representation is displayed to the user via the user interface. The system also includes a thumbnail trend view providing a graph of data elements used to provide the patient-related clinical data value shown in the graphical summary representation. The thumbnail trend view is displayed via the user interface upon a positioning of a cursor over the graphical summary representation. The system further includes an originating data view retrieving and displaying, via the user interface, a source document corresponding to at least one data element on the graph shown in the thumbnail trend view. The originating data view is displayed via the user interface upon a selection of the at least one data element on the graph shown in the thumbnail trend view.

Certain embodiments provide a method for graphical, multi-level information display of patient clinical information to a user. The method includes generating a user interface providing clinical content to a user and accepting user input with respect to clinical content. The method also includes providing a graphical summary representation of a patient-related clinical data value. The graphical summary representation has one or more visible characteristics indicating an importance of the patient-related clinical data value. The graphical summary representation is displayed to the user via the user interface. The method further includes providing a thumbnail trend view including a graph of data elements used to provide the patient-related clinical data value shown in the graphical summary representation. The thumbnail trend view is displayed via the user interface upon a positioning of a cursor over the graphical summary representation. The method additionally includes providing an originating data view retrieving and displaying, via the user interface, a source document corresponding to at least one data element on the graph shown in the thumbnail trend view. The originating data view is displayed via the user interface upon a selection of the at least one data element on the graph shown in the thumbnail trend view.

Certain embodiments provide a machine readable medium having a set of instructions for execution on a computing device. The set of instructions, when executed, generate a multi-level information display system graphically representing clinical information for a user. The set of instructions includes a user interface providing clinical content to a user and accepting user input with respect to clinical content. The set of instructions also includes a graphical summary representation of a patient-related clinical data value. The graphical summary representation has one or more visible characteristics indicating an importance of the patient-related clinical data value. The graphical summary representation is displayed to the user via the user interface. The set of instructions also includes a thumbnail trend view providing a graph of data elements used to provide the patient-related clinical data value shown in the graphical summary representation. The thumbnail trend view is displayed via the user interface upon a positioning of a cursor over the graphical summary representation. The set of instructions further includes an originating data view retrieving and displaying, via the user interface, a source document corresponding to at least one data element on the graph shown in the thumbnail trend view. The originating data view is displayed via the user interface upon a selection of the at least one data element on the graph shown in the thumbnail trend view.

BRIEF DESCRIPTION OF SEVERAL VIEWS OF THE DRAWINGS

FIG. 2 shows an example adaptive user interface in accordance with an embodiment of the present invention.

FIG. 3 depicts an example mobile device including a user interface, such as the user interface described in relation to FIG. 2.

FIG. 4 illustrates an example use case of an adaptive, work-centered user interface in perinatal care in accordance with an embodiment of the present invention.

FIG. 6 illustrates a multi-resolution information display system in accordance with an embodiment of the present invention.

Figure 1:
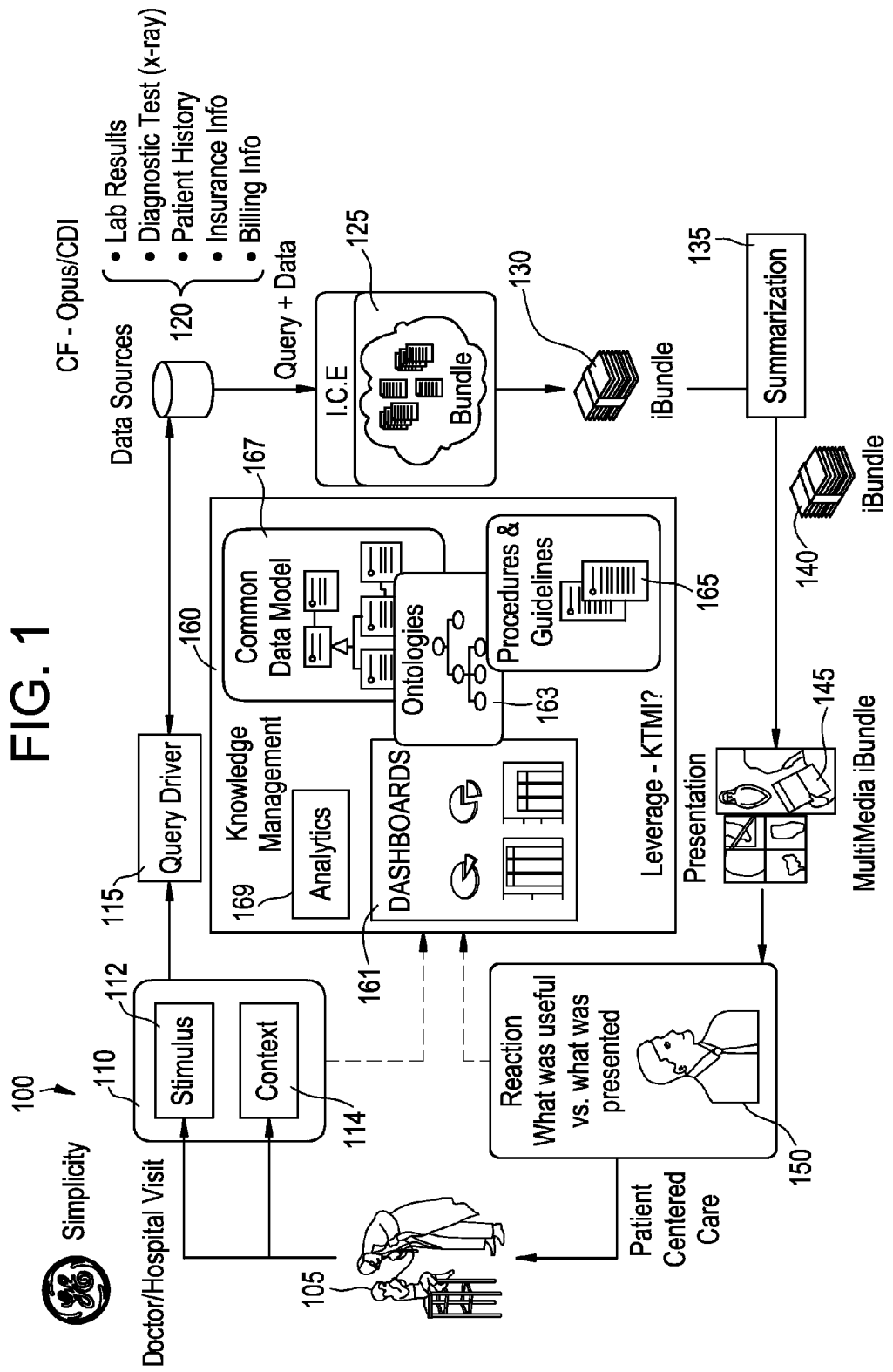
FIG. 1 illustrates a workflow for providing adaptive, work-centered healthcare services in accordance with certain embodiments of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide a simplified data visualization model that assists a user in navigating information from a high level (e.g., summarized) view to a low level (e.g., detailed data elements) view, while maintaining a context for the user. Certain embodiments provide a user interface and data display facilitating interaction between the user and the data on a plurality of detail/access levels.

This approach uses a rules engine to determine a threshold and trending of discreet clinical elements and manifests those results in the form of a geometric representation employing visual features (e.g., size and/or color) of the representation/shape to represent a relevance and an urgency of the information. In an example embodiment, embedded within this geometric representation is a link to a thumbnail view of the trended data element enabling the user to interact with historical readings of these elements (e.g., a trend). Interacting with the thumbnail view enables the user to see an expanded view of the trend along with individual data points that link back to and display the original source for that data element, for example.

Rather than simply posting all available medical information on a screen for user review without determining a correct resolution of data for a clinician to make an informed decision, a clinician is offering easy access to several levels of data. Such access to multiple levels of data enables new insight into the value of the data, the trend of the data, and the contextual view of the original data capture point, for example. This type of data display allows the clinician to spend more time treating the patient than spending time sifting through and synthesizing the information.

Certain embodiments provide, for example, a four-level process for unfolding and visualizing data. While other embodiments can provide differing levels of detail, examples herein use a four-level system and methodology for purposes of example illustration only. For example, a four-level representation can include: 1) a summarized view, 2) a thumbnail trend view, 3) a full trend view, and 4) an originating data view.

A summarized view is a dynamic geometric representation of individual data elements that is characterized by thresholding. For example, a blood pressure within a normal range is displayed as a small green box. As the blood pressure exceeds the normal range, the representation becomes a larger box, and the color of the box migrates towards the red end of the spectrum, for example.

A thumbnail trend view provides a greater level of context regarding a specific data element. The thumbnail trend view displays a thumbnail graph of historical values, for example. In certain embodiments, range information is provided regarding the trend of historical values upon a mouse-over and/or other similar cursor event, for example.

A full trend view provides a full view of the trend information provided in the thumbnail view. For example, on a mouse click and/or other similar cursor event, a full view of the trend view is displayed. Within this view, the user has the ability to drag and drop other data elements onto the graph to allow for comparison of the values between the data elements. Such trend viewing and data comparison helps provide a richer understanding of possible interactions between data elements, for example.

An originating data view displays an original data source of a data point on the trend graph. For example, by mouse clicking and/or otherwise positioning a cursor on a data point on the graph in the full trend view, the system displays the original data source complete with a full data context.

Thus, certain embodiments provide innovative systems and methods to display and interact with individual data elements as well as provide trending and the ability to retrieve the original data source in a simple methodology, resulting in increases in both efficiency and effectiveness for the clinician.

Healthcare information systems are most effective when users are able to find and make use of relevant information across a timeline of patient care. An adaptive user interface can leverage semantic technology to model domain concepts, user roles and tasks, and information relationships, for example. Semantic models enable applications to find, organize and present information to users more effectively based on contextual information about the user and task. Applications can be composed from libraries of information widgets to display multi-content and multi-media information. In addition, the framework enables users to tailor the layout of the widgets and interact with the underlying data.

In an example, a new level of adaptive user interface design is achieved by taking advantage of semantic Web technology. Domain concepts and relationships are characterized in a hierarchy of ontologies, associated with upper level ontological constructs that enable adaptive reasoning and extensibility.

Thus, certain embodiments offer adaptive user interface capabilities through use of a controller that can "reason" about metadata in an ontology to present users with a work-centered application tailored to individual needs and responsive to changes in a work domain. Targeted information can be delivered from "external" data in an application context-sensitive manner In human-computer interaction, user interface data, events, and frequencies can be displayed, recorded, and organized into episodes. By computing data positioning on the screen, episode frequencies, and implication relations, certain example embodiments can automatically derive application-specific episode associations and therefore enable an application interface to adaptively provide just-in-time assistance to a user. By identifying issues related to designing an adaptive user interface, including interaction tracking, episodes identification, user pattern recognition, user intention prediction, and user profile update, an interface is generated that can act on a user's behalf to interact with an application based on certain recognized plans. To adapt to different users' needs, the interface can personalize its assistance by learning user profiles and disease-specific workflows, for example.

In certain embodiments, an adaptive user interface system includes a plurality of widgets to offer a complete view of an entire patient medical record in a user-specific, role-specific, and/or disease-specific manner. In certain embodiments, a user interface can also be configured to provide operation views of data, financial views of data, and also serve as a dashboard for any type of data aggregation, for example.

Certain embodiments provide an adaptive, work-centered user interface technology software architecture. The architecture uses an ontology modeling approach to characterize a work domain in terms of "work-centered" activities as well as computation mechanisms that achieve an implementation supporting those activities. The architecture also provides adaptive interaction, both user directed and automated, in the work-centered characterization and presentation mechanisms of the user interface to enterprise-level applications.

A work-centered solution helps provide an integrated and tailored system that offers support to work in a flexible and adaptable manner by customizing user interaction according to the situated context in which work is accomplished. Under a work-centered approach, an understanding of the overall targeted work domain is developed. For example, questions used to develop an understanding of the work domain can include what the work domain encompasses, what the goals of work are, who participates in the work domain, and how the participants achieve the goals of the work domain, given a local context. The understanding of the work domain can be used to characterize and, thus, support participants' day-to-day activities.

FIG. 1 illustrates a workflow 100 for providing adaptive, work-centered healthcare services in accordance with certain embodiments of the present invention. The workflow 100 includes a patient visit 105 to a doctor, hospital, clinic, etc. From the patient visit 105, a query 110 is generated by a clinician such as an examining physician, a nurse, etc. The query 110 can include a stimulus 112 observed and a patient context 114, for example. The query 110 is passed to a query driver 115. The query driver 115 can query one or more data source 120 and/or a knowledge management subsystem 160, for example. Data source(s) 120 can include one or more of lab results, diagnostic tests (e.g., x-ray, magnetic resonance image, ultrasound, etc.), patient history, insurance information, billing information, etc.

In certain embodiments, the query driver 115 can include and/or be in communication with a Query Enhancement Engine ("QUEEN"). Information may be represented in a plurality of formats including text (e.g., reports and papers), tables (e.g., databases), images (e.g., x-ray and computed tomography scans), and video (e.g., surgical procedures). Furthermore, information often reside on different systems and are stored and/or computed in a heterogeneous environment.

The Query Enhancement Engine can be used for retrieving information from disparate information sources 120 based on an information need (e.g., a stimulus 112) and a context 114. First, based on the original query 110 and context 114, QUEEN determines which information source(s) 120 are most appropriate for retrieving the requested information by consulting an information registry.

Once candidate information source(s) 120 have been identified, the query 110 is generated (by the Query Enhancement Engine 115) and passed to the information source 120 for retrieval. Different data repositories (file systems, databases, etc) utilize different mechanisms for retrieving data within them. The information source 120 encapsulates these retrieval mechanisms.

To improve the precision of retrieval results, it is sometimes beneficial to modify the query prior to retrieval. Query enhancement may involve adding additional terms to a query to improve results. Query refinement may involve removing or substituting terms to a query to improve performance. QUEEN may request information using an initial query and then enhance or refine the query to improve performance, for example.

The query 110 is combined with data from the one or more data source 120 and provided to an information composition engine ("ICE") 125 to compile or bundle data from the data source(s) 120 in response to the query 110. The ICE 125 can bundle information for presentation from multiple, heterogenous data sources 120.

For example, for a given information need, several different types of information may be desirable for the particular task at hand to form a semantically meaningful bundle of information. A bundle includes one or more types of information (e.g., patient history and lab results). Organizing the various informational items into semantic units is referred to as information composition or bundling. The ICE 125 is responsible for composing the retrieved information from the data source(s) 120 together into a bundle that is meaningful to the user. Bundles may be composed based on the semantic needs of the user, and may also be driven by user preferences, and/or other knowledge appropriate to the domain, for example.

In certain embodiments, the ICE 125 uses Composers to compose the information retrieved from the data source(s) 120. Composers employ Composition Decision Logic ("CDL"), for example, to compose the information. Some examples of CDL include aggregation elimination of redundant information, lightweight summarization of information, and fusion of results, for example.

The ICE 125 then produces a bundle 130 including relevant information composed and tailored for a requesting user based on context information 114 from the query 110. The bundle 130 is passed to the summarization engine 135. The summarization engine 135 provides multi-document summarization for the content of the bundle 130. Summarization will be described further below.

A revised bundle 140, annotated with summaries from the summarization engine 135, is used to generate a presentation 145. The presentation can include a multimedia bundle of text, video and images returned from a metadata search of the data source(s) 120 and including contextual summaries from the summarization engine 135. A user can drill down into details through the presentation 145. A user, such as a physician and/or nurse, can use information from the presentation 145 to further diagnose and/or treat the patient. A user's reaction and/or other feedback 150 from the presentation 145 information can be provided back to the knowledge management subsystem 160 for subsequent use.

The knowledge management subsystem 160 will now be described in further detail. The knowledge management subsystem 160 includes one or more tools and/or additional information to assist the query driver 115 to form a query to extract relevant information from the data source(s) 120. Query 110 information, such as stimulus 112 and context 114, can be input to the knowledge management subsystem 160 to provide relevant tools and/or information for the query driver 115. Alternatively and/or in addition, clinician reaction and/or other feedback 150 can be fed back into the subsystem 160 to provide further information and/or improve further results from the knowledge management subsystem 160.

As shown, for example, in FIG. 1, the knowledge management subsystem 160 includes one or more dashboards 161, one or more ontologies 163, procedures and guidelines 165, a common data model 167, and analytics 169. The knowledge management subsystem 160 can provide a Knowledge and Terminology Management Infrastructure ("KTMI") to the workflow 100. An ontology 163 details a formal representation of a set of concepts within a domain and the relationships between those concepts. The ontology 163 can be used to define a domain and evaluate properties of that domain. The common data model 167 defines relationships between disparate data entities within a particular environment and establishes a context within which the data entities have meaning. The common data model 167 provides a data model that spans applications and data sources in the workflow 100 and defines data relationships and meanings within the workflow 100. Using the analytics 169, for example, the subsystem 160 can access dashboard(s) content 161, ontology(ies) 163, and procedures/guidelines 165 based on a common data model 167 to provide output to the query driver 115.

The activity of summarization engine 135 will now be described in further detail. Multi-document summarization is an automatic procedure aimed at extraction of information from multiple texts written about the same topic (e.g., disease across multiple patients). A resulting summary report allows individual users, such as examining physicians, nurses, etc., to quickly familiarize themselves with information included in a large cluster of documents. Thus, the summarization engine 135 can complement the ICE 125 to summarize and annotate content for ease of reference, for example.

Multi-document summarization creates information reports that are more concise and comprehensive than a review of the raw data. Different opinions are put together and outlined to describe topics from multiple perspectives within a single document. While a goal of a brief summary is to simplify an information search and reduce time by pointing to the most relevant source documents, a comprehensive multi-document summary should itself contain the requested information, hence limiting the need for accessing original files to cases when refinement is required. Automatic summaries present information extracted from multiple sources algorithmically, without any editorial touch or subjective human intervention, in an attempt to provide unbiased results.

However, multi-document summarization is often more complex than summarizing a single document due to thematic diversity within a large set of documents. A summarization technology aims to combine the main document themes with completeness, readability, and conciseness. For example, evaluation criteria for multi-document summarization developed through Document Understanding Conferences, conducted annually by the National Institute of Standards and Technology, can be used.

In certain embodiments, the summarization engine 135 does not simply shorten source texts but presents information organized around key aspects of the source texts to represent a wider diversity of views on a given topic. When such quality is achieved, an automatic multi-document summary can be used more like an overview of a given topic.

Multi-document summary criteria can include one or more of the following: a clear structure, including an outline of the main content, from which it is easy to navigate to full text sections; text within sections is divided into meaningful paragraphs; a gradual transition from more general to more specific thematic aspects; good readability; etc. with respect to good readability, the automatic overview can show, for example, no paper-unrelated "information noise" from the respective documents (e.g., web pages); no dangling references to subject matter not mentioned or explained in the overview; no text breaks across a sentence; no semantic redundancy; etc.

In certain embodiments, a summarization approach includes three steps: 1) segmentation, 2) clustering/classification, and 3) summary generation. An initial text segmentation is performed by dividing or "chunking" a document into paragraphs based on existing paragraph boundaries. Subtitles and one-line paragraphs can be merged, for example. When no paragraph boundaries are present, then chunking can be done by dividing after ever N words (e.g., every 20 words), for example.

For clustering, one or more natural language processing ("NLP") techniques can be applied to measure similarity between two collections of words, for example. For example, paragraphs including similar strings of words (e.g., N-grams) are identified, and a similarity metric is defined to determine whether two passages are similar. For example, a similarity metric can provide an output resembling a cosine function (e.g., results closer to a value of one indicate greater similarity). Passage similarity scores can be computed for all pairs of passages using these metrics.

In certain embodiments, it is computationally expensive to look at all combinations of clusters when there are many passages. Therefore, clustering can be performed in two steps: seed clustering and classification. In seed clustering, a complete-link algorithm can be used until a target number of clusters are found. For example, a target number of clusters can be equal to log(number of documents). In classification, remaining passages are then classified by finding a best matching seed cluster. If a passage has no similarity, it is placed in a trash cluster.

For summary generation, a most characteristic paragraph is then taken from each cluster to form a "meta document." A single document summarizer is then used to create a "summary" for the entire collection. The summary is bundled with the information and provided as the bundle 140.

As an example of the workflow 100 in action, suppose that, prior to performing surgery on a patient, a physician wants to know what allergies a patient has. Information about a patient's allergies may be stored in different systems using a combination of document repositories, file systems, and databases 120. Using the ICE 125, a variety of information about the patent's allergies is found and bundled and presented to the physician. Some of the information may be buried within paragraphs in some documents, while other information is found in database tables, for example. When a system's databases have been exposed (e.g., through a Connectivity Framework), the ICE 125 and its QUEEN engine can connect to the database 120 to query for information. When a database is not available for a particular system, the document repository for that system can still be searched. The document summarizer 135 can be used to provide summaries of documents retrieved and to cluster related passages from documents retrieved to pull in related patient information. The information is organized into a bundle 140 before being delivered to the user. The information may be organized based on information type, semantics, information relevance, and the confidence score from the underlying repository, for example. The information may be graphically provided to a user via a multi-level dynamic clinical display, for example.

In certain embodiments, the workflow 100 supports a user by continually searching for relevant information from connectivity framework components using a query generation engine 115. Subsequently, these results are classified and bundled through an information composition engine 125 that transforms the information for appropriate presentation to the user.

In certain embodiment, an adaptive user interface ("UI") design is achieved by taking advantage of semantic web technology. For example, domain concepts and relationships are characterized in a hierarchy of ontologies, associated with upper level ontological constructs that enable adaptive reasoning and extensibility.

A core ontology can be derived from one or more work-centered design principles. For example, an effective interface can display information that represents a perspective that a user needs on a situated work domain to solve particular types of problems. As another example, information that is the most important to the user in the current work context can be displayed in a focal area to engage the user's attention. Referential information can be offered in a periphery of a display to preserve context and support work management. As a further example, a user's own work ontology (e.g., terms and meaning) should be the primary source for information elements in the interface display.

Thus, certain embodiments provide adaptive user interface capabilities through use of a controller that can "reason" about metadata in an ontology to present users with a work-centered application tailored to individual needs and responsive to changes in the work domain. Such user interface capabilities help obviate problems associated with browsing "external" data that a connectivity framework can access by offering an interface to deliver targeted information in an application context-sensitive manner.

In human-computer interaction, user interface data, events, and frequencies can be displayed, recorded, and organized into episodes. By computing data positioned on a display screen, episode frequencies, and implication relations, application-specific episode associations can be automatically derived to enable an application interface to adaptively provide just-in-time assistance to a user. By identifying issues related to designing an adaptive user interface, including interaction tracking, episodes identification, user pattern recognition, user intention prediction, and user profile update, for example, the interface can act on a user's behalf to interact with an application based on certain recognized plans. To adapt to different users' needs, the interface can personalize its assistance by learning user profiles and disease-specific workflows, for example.

Figure 2:
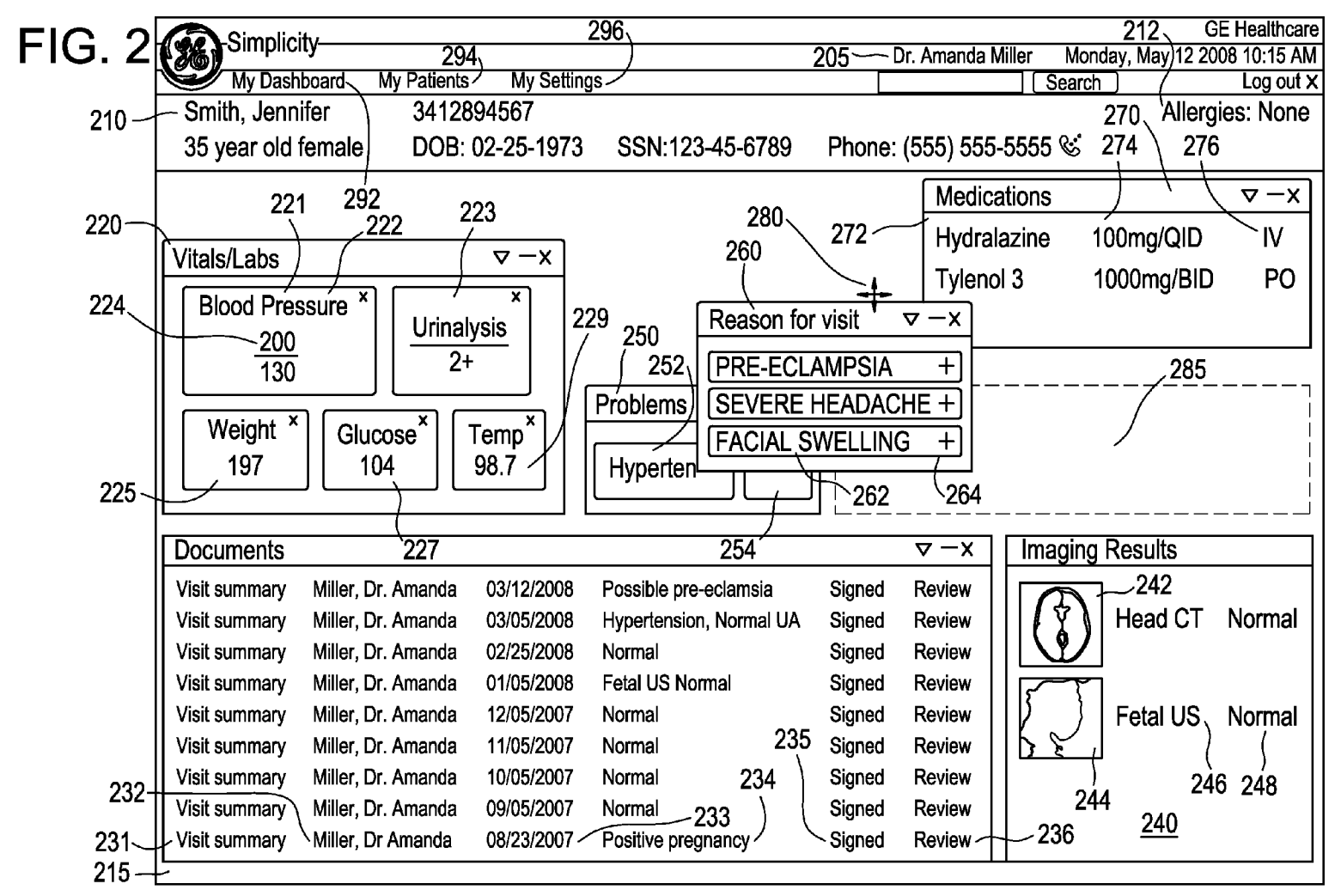

FIG. 2 shows an example adaptive user interface ("UI") 200 in accordance with an embodiment of the present invention. The UI 200 includes a login and user identification area 205, a patient identification area 210, an alert 212, and a widget display area 215. The user identification area 205 identifies the user currently logged in for access to the UI 200. The patient identification area 210 provides identification information for a target patient, such as name, identification number, age, gender, date of birth, social security number, contact information, etc. The alert 212 can provide patient information for the attention of the user, such as an indication that the patient has no allergies. The widget display area 212 includes one or more widgets positionable by a user for use via the UI 200.

For example, as shown in FIG. 2, the widget display area 212 includes widgets 220, 230, 240, 250, 260, 280. Widgets can provide a variety of information, clinical decision support, search capability, clinical functionality, etc. As shown, for example, in FIG. 2, the widget 220 is a vitals/labs widget. The vitals widget 220 provides a visual indicator of one or more vital signs and/or lab test results for the patient. For example, indicators can include blood pressure 221, urinalysis 223, weight 225, glucose 227, and temperature 229. Each indicator includes a type and a value. For example, the blood pressure indicator 221 includes a type 222 (e.g., blood pressure) and a value 224 (e.g., 200 over 130). Each indicator 221, 223, 225, 227, 229 has a certain color and/or a certain size to indicate an importance of the constituent information from the indicator. For example, the blood pressure indicator 221 is the largest sized indicator in the widget 220, visually indicating to a user the relative importance of the blood pressure reading 221 over the other results. Urinalysis 223 would follow as next in importance, etc. As another example, blood pressure 221 is colored red, urinalysis 223 is colored orange, weight 225 is colored yellow, and both glucose 227 and temperature 229 are colored green. The color can be used to indicate a degree of severity or importance of the constituent value. For example, blood pressure 221, colored red, would carry the most importance, urinalysis 223, colored orange, would be next in importance, etc. Thus, indicator size and/or color can be used together and/or separately to provide the user with an immediate visual indication of a priority to be placed on investigation of patient vitals and lab results. In certain embodiments, selection of an indicator retrieves data, results, and/or document(s) used to generate the information for the indicator.

Widget 230 provides a list of clinical documents related to the patient, such as encounter summaries, reports, image analysis, etc. Document information can include a document type 231, a document author 232, a document date 233, an evaluation from the document 234, a document status 235, and an action for the document 236. For example, an entry in the document widget 230 can be of visit summary type 231, generated by author 232 Dr. Amanda Miller, on a date 233 of Mar. 12, 2008, diagnosing 234 possible pre-eclampsia, with a status 235 of signed, and an action 236 of review. A user can select a document entry to retrieve and display the actual document referenced in the widget 230.

Widget 240 provides one or more imaging studies for review by the user. The imaging studies widget 240 includes one or more images 244 along with an imaging type 246 and an evaluation 248. For example, as shown in FIG. 2, the widget 240 includes a head CT evaluated as normal and a fetal ultrasound image evaluated as normal.

Widget 250 provides a visual representation of one or more problems 252, 254 identified for the patient. Similar to the vitals widget 220, the problem indicators 252, 254 can have a certain color and/or a certain size to indicate an importance of the constituent information from the problem indicator. For example, in the hypertension problem indicator 242 is colored red and is larger than the other problem indicator 254. Thus, indicator size and/or color can be used together and/or separately to provide the user with an immediate visual indication of a priority to be placed on investigation of patient problems. In certain embodiments, selection of a problem indicator retrieves data, results, and/or document(s) used to generate the information for the indicator.

Widget 260 provides one or more reasons for a patient's visit to the user. The reason for visit widget 260 includes a reason 262 and an icon 264 allowing the user to expand the reason 262 to view additional detail or collapse the reason 262 to hide additional detail. The reasons 262 can be color coded like the indicators from widgets 220, 250 to provide a visual indication of priority, significance, severity, etc.

Widget 270 provides a listing of medications prescribed to the patient. The medications widget 270 includes a type 272 of medication, a quantity 274 of the medication, and a delivery mechanism 276 for the medication. In certain embodiments, selection of a medication can pull up further detail about the medication and its associated order, for example.

As shown, for example, in FIG. 2, a user can manipulate a cursor 280 to select a widget and position the widget at a location 285. Thus, a user can select widgets for display and then arrange their layout in the widget display area 215 of the UI 200. Alternatively and/or in addition, the user can reposition widgets in the widget display area 215 to modify the UI 200 layout. For example, using the cursor 280, the user can place the reason for visit widget 260 in a certain spot 285 on the widget display area 215.

The UI 200 can also provide one or more links to other clinical functionality, such as a user dashboard 292, a patient list 294, a settings/preferences panel 296, and the like.

Certain embodiments allow healthcare information systems to find and make use of relevant information across a timeline of patient care. For example, a search-driven, role-based interface allows an end user to access, input, and search medical information seamlessly across a healthcare network. An adaptive user interface provides capabilities through a work-centered interface tailored to individual needs and responsive to changes in a work domain, for example. Semantic technology can be leveraged to model domain concepts, user roles and tasks, and information relationships. The semantic models enable applications to find, organize and present information to users more effectively based on contextual information about the user and task. Components forming a framework for query and result generation include user interface frameworks/components for building applications; server components to enable more efficient retrieval, aggregation, and composition of information based on semantic information and context; and data access mechanisms for connecting to heterogeneous information sources in a distributed environment.

A variety of user interface frameworks and technologies can be used to build applications including, Microsoft® ASP.NET, Ajax®, Microsoft® Windows Presentation Foundation, Google® Web Toolkit, Microsoft® Silverlight, Adobe®, and others. Applications can be composed from libraries of information widgets to display multi-content and multi-media information, for example. In addition, the framework enables users to tailor layout of the widgets and interact with underlying data.

Healthcare information can be distributed among multiple applications using a variety of database and storage technologies and data formats. To provide a common interface and access to data residing across these applications, a connectivity framework ("CF") is provided which leverages common data and service models ("CDM" and "CSM") and service oriented technologies, such as an enterprise service bus ("ESB") to provide access to the data.

FIG. 3 depicts example mobile devices including a user interface, such as the user interface described in relation to FIG. 2. As shown in FIG. 3, a mobile device 310 can include a graphical user interface 320, a navigation device 330, and one or more tools 340 for interaction with the content of the interface 320, for example. The mobile device 310 can include a cellular phone, personal digital assistant, pocket personal computer, and/or other portable computing device. The mobile device 310 includes a communication interface to exchange data with an external system, for example.

A combination of mobile services and Web services can be used for delivery of information via the mobile device 310. Using Mobile Web Technology, portability, ubiquitous connectivity, and location-based services can be added to enhance information and services found on the Web. Applications and various media do not need to reside in separate silos. Instead, applications on these devices 310 can bring together elements of Web 2.0 applications, traditional desktop applications, multimedia video and audio, and the mobile device (e.g., a cell phone), for example. Using an adaptive user interface architecture, widgets can be designed for mobile devices to enable users to create or consume important clinical information whenever and wherever they need it, for example.

FIG. 4 illustrates an example use case of an adaptive, work-centered user interface 400 in perinatal care in accordance with an embodiment of the present invention. In the example of FIG. 4, Patricia Smith, a 35-year old pregnant female, is in her 34th week of her third pregnancy. Throughout the course of her care, Patricia has had the typical workup, including initial lab studies, vitals, a three-dimensional ("3D") fetal ultrasound, and other routine tests. With the exception of her gestational diabetes, Patricia has had a normal pregnancy, and all indications are that she'll deliver a healthy baby boy at full term.

At her 34-week appointment, however, Patricia's obstetrician/gynecologist becomes somewhat concerned at her blood pressure, which is high compared to previous readings, at 145/95. Dr. Amanda Miller orders an electrocardiogram ("EKG") and a urinalysis ("UA") test. Although Patricia's EKG shows a normal sinus rhythm, her UA comes back with trace amounts of Albumin, suggestive of pre-eclampsia. Dr. Miller asks Patricia to set up her next appointment for one week from today to monitor her blood pressure and kidney function.

The following week, Patricia's blood pressure is higher than the previous value (150/98) and Dr. Miller orders another urinalysis. The UA comes back positive again, but at about the same level as before. Dr. Miller feels it's prudent to continue the weekly visits until her blood pressure comes down to normal levels. She also mentions to Patricia that one warning sign of eclampsia is a sudden, severe headache, and, if she experiences one, she should go directly to the Emergency Department for care.

At her son's fifth birthday party over the weekend, Patricia comes down with a severe headache. Tom, her husband, immediately takes her to the Emergency Department ("ED") at the local hospital. The ED staff access all of Patricia's medical records via a longitudinal timeline record, for example, and become informed about all of the aspects of her case. With Patricia's blood pressure ("BP") skyrocketing at 200/130, the ED doc orders a series of tests—UA, EKG, Chem Panel, and a Head CT. Both the Chem Panel and Head CT come back normal but, just as Dr. Miller feared, the UA shows and elevated level of Albumin (2+). Given the result of the tests and Patricia's condition, the ED doc and Dr. Miller decide the best course of action is to deliver the baby via a C-section as soon as Patricia's blood pressure comes under control. She is administered Hydralazine (through her IV) to control the hypertension and Tylenol 3 for her headache, and is transported to surgical holding.

The C-section was a success, and Patricia and Tom are the proud parents of Evan, a six-pound, four-ounce healthy baby boy. After a week's stay, both Patricia and Evan are discharged from the hospital. Both Patricia and Evan are examined a week later at Dr. Miller's office. Patricia's albumin and blood pressure have returned to normal, as has her blood glucose level.

Using the user interface 400, Dr. Miller can easily review, enter, and modify Patricia's progress, lab results, vitals, etc., based on an identification of the patient 405. The UI 400 shows Patricia's vitals 410 and visually indicates through a large, red icon 415 that Patricia's blood pressure is of concern. Additionally, abnormal urinalysis results 417 are visually highlighted to the physician. Clinical details 410 of the urinalysis can be easily reviewed, with key results highlighted to indicate positive 425 or negative 427 results. Dr. Miller can review the radiology 430 and cardiology 440 studies she ordered for Patricia and can check documents 450, including previous progress notes 455 to evaluate Patricia's progress. Dr. Miller (and/or an assisting nurse, for example) can also enter and review Patricia's reasons for visiting the hospital 460. After prescribing the Hydralazine and Tylenol 3, Dr. Miller can verify the dosage and delivery methods and modify them following the C-section via a Medications widget 470. If Dr. Miller has further questions and/or wants to search for additional information, a search field 480 allows her to do so.

Figure 5A:
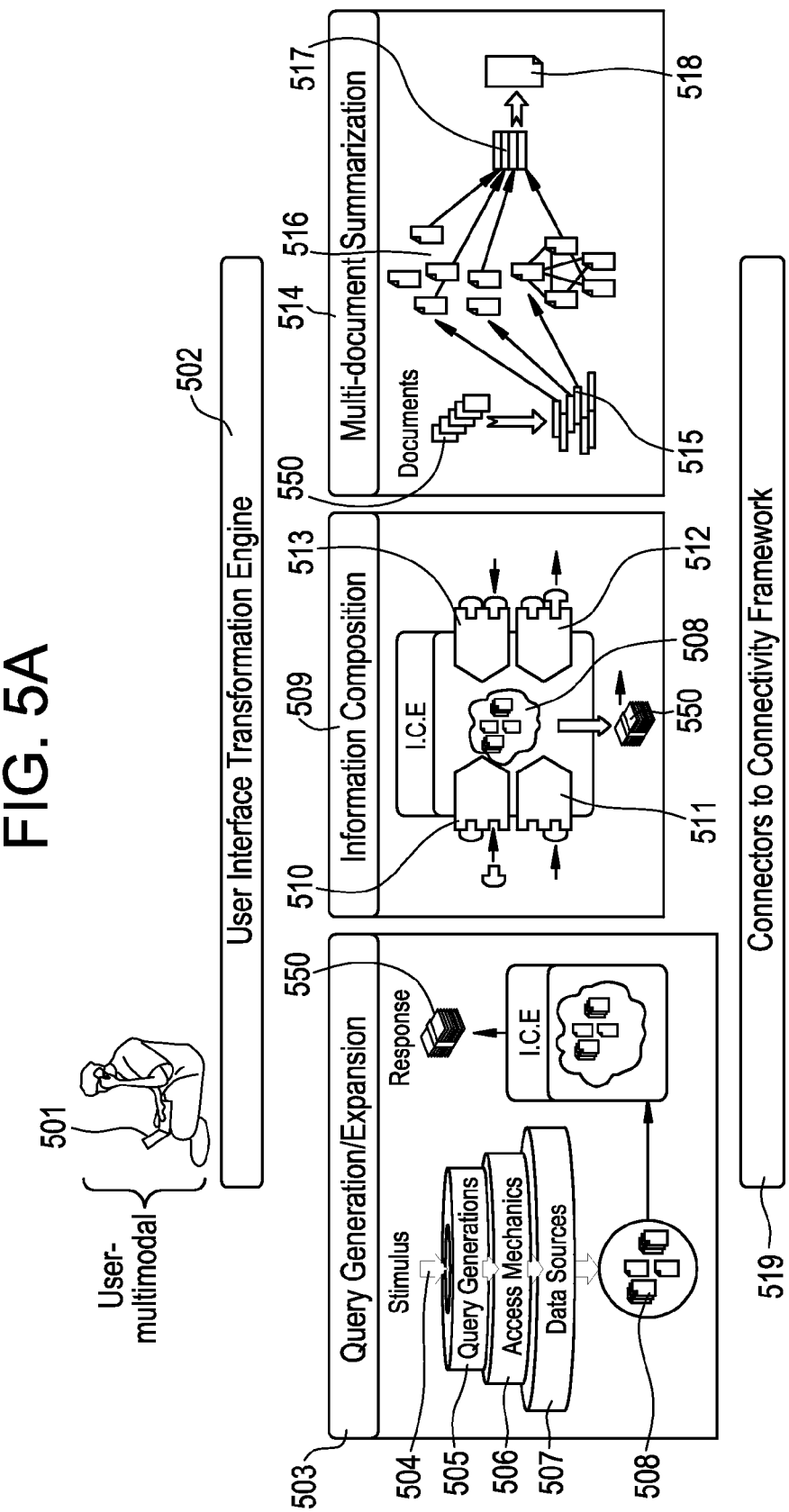
FIG. 5 depicts a user interface architecture in accordance with certain embodiments of the present invention.
Figure 5B:
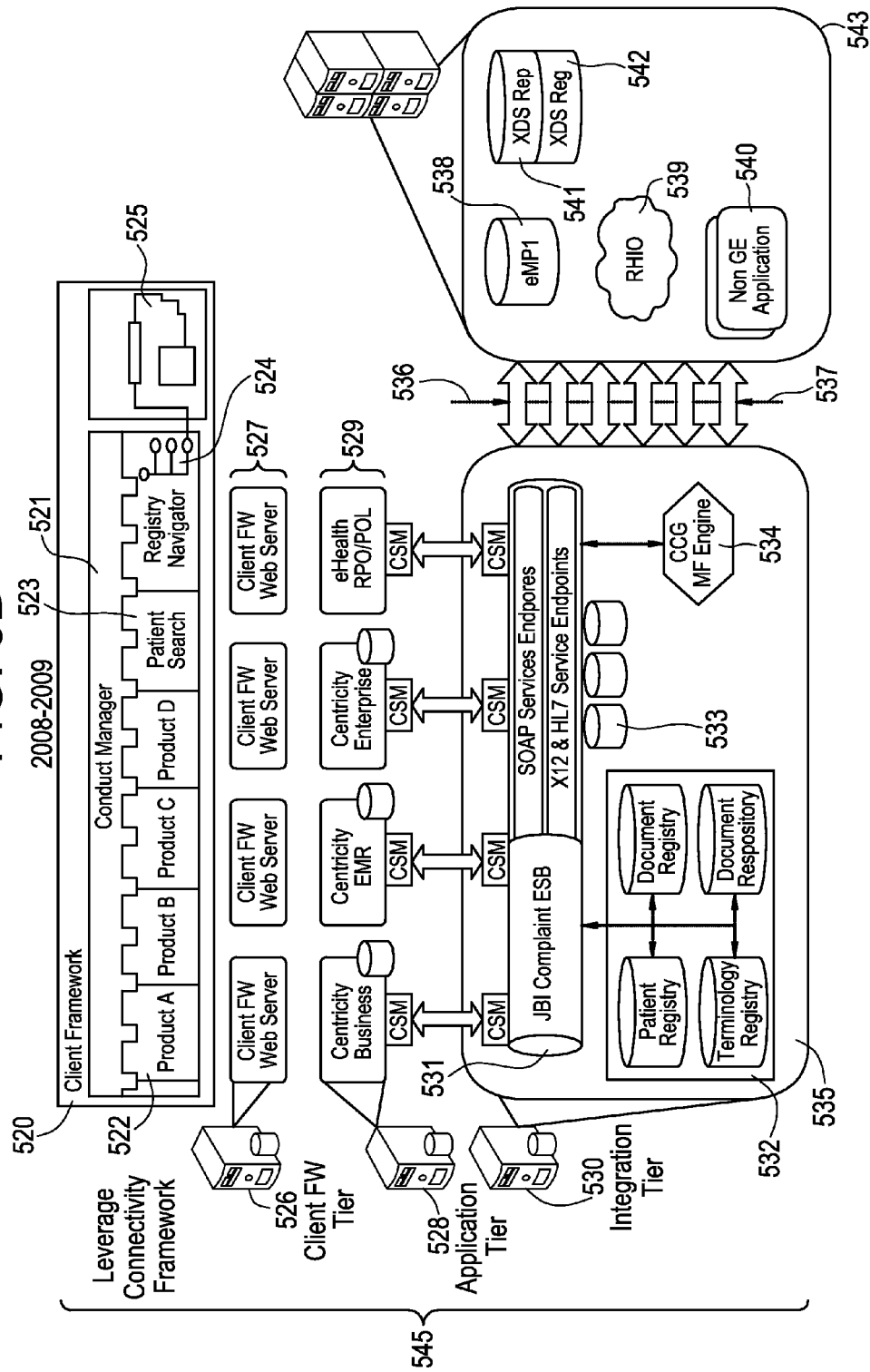

FIG. 5 depicts a user interface architecture 500 in accordance with certain embodiments of the present invention. The architecture 500 includes a user interface transformation engine 502, a query generation/expansion engine 503, an information composition engine 509, a multi-document summarization engine 514, and one or more connectors 519 to a connectivity framework 545. The components of the architecture 500 are accessible by a user via a user interface 501 on a processing device, such as a computer or handheld device. The user can submit a query for information via the user interface 501, for example. The query can also be automatically generated based on one or more widgets displayed on the interface 501 and/or other application/parameter information configured with respect to the interface 501 that triggers a query for updated information, for example.

The query generation/expansion engine 503 includes a stimulus 504, one or more query generators 505, and one or more access mechanisms 506 to search one or more data source 507 to produce a query and collected documents 508. The query and collected documents 508 are passed to the information composition engine 509 that includes applications 510, 511, 512, 513 that process and apply cognitive reasoning, for example, to organize the query and collected documents 508 into one or more units meaningful to a requesting user based on one or more of semantic guidelines, user preferences, and domain-related information, for example. A toolset including composers can employ Composition Decision Logic ("CDL"), such as aggregation, elimination of redundant information, lightweight summarization of information, and fusion of results, to compose the information. Applications can include one or more data driven applications 510, enterprise application interfaces 511, task/process driven applications 512, and data structure specific applications 513, for example. The applications 510, 511, 512, and/or 513 can include one or more templates related to new data types, new data structures, domain specific tasks/processes, new application interfaces, etc. Composition and processing of the query and collected documents 508 produces a bundle 550 of information in response to a user query.

The multi-document summarization engine 514 receives the bundle 550 of documents and segments the documents into passages 515. The passages 515 are clustered based on similar concepts 516. A meta-document 517 is then formed from the concepts 516. A summary 518 is generated from the meta-document 517. Query results 550, the meta-document 517, and/or the meta-document summary 518 can be provided to the user via the user interface 501. Information 550, 517, and/or 518 can be provided textually and/or graphically, such as via a graphical representation of the data provided in a multi-resolution clinical data display widget including a capability to drill down into deeper levels of trend and document information via the widget.

Via connectors 519 to a connectivity framework 545, the user interface 501 and its engines 503, 509, 514 can send and receive information in response to user query via the interface 501, for example. For example, the query engine 503 can access the connectivity framework 545 to query one or more data sources 507.

The connectivity framework 545 includes a client framework 520. The client framework 520 includes a context manager 521 for one or more products 522, a patient search 523, a registry navigator 524, and a viewer 525. Thus, in certain embodiments, the connectivity framework 520 can facilitate viewing and access to information via the user interface 501 and apart from the user interface 501. Via the connectivity framework 545, the query engine 503 and/or other parts of the user interface 501 can access information and/or services through a plurality of tiers.

Tiers can include a client framework tier 526, an application tier 528, and an integration tier 530, for example. The client framework tier 526 includes one or more client web servers 527 facilitating input and output of information, for example. The applicant tier 528 includes one or more applications 529 related to enterprise and/or departmental usage such as business applications, electronic medical records, enterprise applications, electronic health portal, etc. The integration tier 530 includes a consolidated interoperability platform server 535 in communication with customer information technology ("IT") 543 via one or more factory 536 and/or custom 537 interfaces, such as default and/or customized interfaces using a variety of message formats such as a web service ("WS"), X12, Health Level Seven ("HL7"), etc. The consolidated interoperability platform 535 can communicate with the one or more applications 529 in the application tier 528 via a common service model ("CSM"), for example.

As shown, for example, in FIG. 5, the consolidated interoperability platform 535 includes an enterprise service bus ("ESB") 531, a collection of registries, data, and services 532, configuration information 533, and a clinical content gateway ("CCG") interface engine 534, for example. The ESB 531 can be a Java business intelligence ("JBI") compliant ESB, for example. The ESB 531 can include one or more endpoints or locations for accessing a Web service using a particular protocol/data format, such as X12, HL7, SOAP (simple object access protocol), etc., to transmit messages and/or other data, for example. Using a CSM, the ESB 531 facilitates communication with the applications 529 in the application tier 528, for example. Via the ESB 531, information in the registries, data and services repository 532 can be provided to the applicant tier 531 in response to a query, for example. Configuration information 533 can be used to specify one or more parameters such as authorized users, levels of authorization for individual users and/or groups/types of users, security configuration information, privacy settings, audit information, etc. The CCG interface engine 531 receives data from the customer IT framework 543 and provides the data to the registries 532 and/or applications 529 in the application tier 531, for example.

As shown, for example, in FIG. 5, the customer IT 543 includes support for a third party electronic message passing interface ("eMPI") 538, support for a regional health information organization ("RHIO") 539, one or more third party applications 540, support for a cross-enterprise document sharing ("XDS") repository 541, support for an XDS registry 542, and the like. Using customer IT 543 in conjunction with the interoperability platform 535, a RHIO gateway and third party application integration can be provided via one or more interfaces to the connectivity framework 545 and/or the query generation/expansion engine 503 of the user interface 501.

The customer IT framework 543 can be organized to provide storage, access and searchability of healthcare information across a plurality of organizations. The customer IT framework 543 may service a community, a region, a nation, a group of related healthcare institutions, etc. For example, the customer IT framework 543 can be implemented with the RHIO 539, a national health information network ("NHIN"), a medical quality improvement consortium ("MQIC"), etc. In certain embodiments, the customer IT 543 connects healthcare information systems and helps make them interoperable in a secure, sustainable, and standards-based manner.

In certain embodiments, the customer IT framework 543 provides a technical architecture, web applications, a data repository including EMR capability and a population-based clinical quality reporting system, for example. The architecture includes components for document storage, querying, and connectivity, such as the XDS registry 542 and repository 541. In certain embodiments, the XDS registry 542 and repository 541 can include an option for a subscription-based EMR for physicians, for example. In certain embodiments, the XDS registry 542 and repository 541 are implemented as a database or other data store adapted to store patient medical record data and associated audit logs in encrypted form, accessible to a patient as well as authorized medical clinics. In an embodiment, the XDS registry 542 and repository 541 can be implemented as a server or a group of servers. The XDS registry 542 and repository 541 can also be one server or group of servers that is connected to other servers or groups of servers at separate physical locations. The XDS registry 542 and repository 541 can represent single units, separate units, or groups of units in separate forms and may be implemented in hardware and/or in software. The XDS registry 542 and repository 541 can receive medical information from a plurality of sources.

Using an XDS standard, for example, in the customer IT framework 543, document querying and storage can be integrated for more efficient and uniform information exchange. Using the customer IT 543, quality reporting and research may be integrated in and/or with an RHIO 539 and/or other environment. The customer IT 543 can provide a single-vendor integrated system that can integrate and adapt to other standards-based systems, for example.

Via the customer IT framework 543, a group of EMR users may agree to pool data at the XDS registry 542 and repository 541. The customer IT framework 543 can then provide the group with access to aggregated data for research, best practices for patient diagnosis and treatment, quality improvement tools, etc.

XDS provides registration, distribution, and access across healthcare enterprises to clinical documents forming a patient EMR. XDS provides support for storage, indexing, and query/retrieval of patient documents via a scalable architecture. Certain embodiments, however, support multiple affinity domains (defined as a group of healthcare enterprise systems that have agreed upon policies to share their medical content with each other via a common set of policies and a single registry) such that each affinity domain retains its autonomy as a separate affinity domain but shares one instance of hardware and software with the other involved affinity domains. The XDS registry 542 and repository 541 can maintain an affinity domain relationship table used to describe clinical systems participating in each affinity domain. Once a request for a document is made, the source of the request is known and is used to determine which document(s) in the repository 541 are exposed to the requesting user, thus maintaining the autonomy of the affinity domain.

In certain embodiments, the XDS registry 542 and repository 541 represent a central database for storing encrypted update-transactions for patient medical records, including usage history. In an embodiment, the XDS registry 542 and repository 541 also store patient medical records. The XDS registry 542 and repository 541 store and control access to encrypted information. In an embodiment, medical records can be stored without using logic structures specific to medical records. In such a manner the XDS registry 542 and repository 541 is not searchable. For example, a patient's data can be encrypted with a unique patient-owned key at the source of the data. The data is then uploaded to the XDS registry 542 and repository 541. The patient's data can be downloaded to, for example, a computer unit and decrypted locally with the encryption key. In an embodiment, accessing software, for example software used by the patient and software used by the medical clinic performs the encryption/decryption.

In certain embodiments, the XDS registry 542 and repository 541 maintain a registration of patients and a registration of medical clinics. Medical clinics may be registered in the XDS registry 542 and repository 541 with name, address, and other identifying information. The medical clinics are issued an electronic key that is associated with a certificate. The medical clinics are also granted a security category. The security category is typically based on clinic type. In certain embodiments, the requests and data sent from medical clinics are digitally signed with the clinic's certificate and authenticated by the XDS registry 542 and repository 541. Patients may be registered in the XDS registry 542 and repository 541 with a patient identifier and password hash. Patients may also be registered in the XDS registry 542 and repository 541 with name, address, and other identifying information. Typically, registered patients are issued a token containing a unique patient identifier and encryption key. The token may be, for example, a magnetic card, a fob card, or some other equipment that may be used to identify the patient. A patient may access the XDS registry 542 and repository 541 utilizing their token, and, in an embodiment, a user identifier and password.

In certain embodiments, design of the user interface architecture 500 is guided by a plurality of factors related to the interactive nature of the system. For example, one factor is visibility of system status. The system can keep users informed about what is going on through appropriate feedback within reasonable time. Additionally, another factor is a match between the system and the "real world." The system can speak the user's language, with words, phrases and concepts familiar to the user, rather than system-oriented terms. For example, information can follow real-world conventions and appear in a natural and logical order. Additionally, with respect to consistency and standards, users should not have to wonder whether different words, situations, or actions mean the same thing. The interface architecture can follow platform conventions, for example.

Another example factor relates to user control and freedom. Users often choose system functions by mistake and need a clearly marked "emergency exit" to leave the unwanted state without having to go through an extended dialogue. Certain embodiments support undo and redo operations related to configuration of system parameters and information query, for example.

Another factor is error prevention. Error-prone conditions can be eliminated, or the system can check for error conditions and present users with a confirmation option before a remedial action is executed. Additionally, certain embodiments can help users recognize, diagnose, and recover from errors. Error messages can be expressed in plain language (e.g., no codes), precisely indicate the problem, and constructively suggest a solution, for example. Even though it is better if the system can be used without documentation, it may be necessary to provide help and documentation. Any such information can be easy to search, focused on the user's task, list concrete steps to be carried out, and not be too large, for example.

With respect to ease of user interaction, the system can reduce or minimize the user's memory load by making objects, actions, and options visible. The user should not have to remember information from one part of the dialogue to another. Instructions for use of the system can be visible or easily retrievable whenever appropriate. Further, accelerators, often unseen by a novice user, can often speed up interaction for an expert user such that the system can cater to both inexperienced and experienced users. In certain embodiments, users can tailor frequent actions. Additionally, displayed dialogues can be configured not to include information that is irrelevant or rarely needed. Every extra unit of information in a dialogue competes with the relevant units of information and diminishes their relative visibility.

Certain embodiments provide visualization strategies with a graphical user interface for disparate data types across large clinical datasets across an enterprise. Thus, design elements can include, for example, institutional components, a single point of access search, one or more components/widgets, one or more medical records grids/forms, scheduling, clinical data results, graphs, task lists, messaging/collaboration components, multi-scale images (e.g., deep zoom), one or more external components, mail, RSS feeds, external Web-based clinical tools (e.g., WebMD), etc. Server components can include, for example, a search engine, a Web server, an active listener, an information composition engine, a query engine, a data aggregator, a document summarizer, profile context management, one or more dashboards (e.g., clinical and administrative), etc.

FIG. 6 illustrates a multi-resolution information display system 600 in accordance with an embodiment of the present invention. The multi-resolution information display system 600 can be implemented as an application, a user interface, a widget within a user interface, etc. The display system 600 can be provided as a thick and/or thin client solution and can be accessible via a workstation, Web browser, handheld device, etc.

The multi-resolution information display system 600 includes a display panel or view 605. The panel 605 includes one or more graphical representations 610 of clinical information relevant to a patient. Each graphical representation 610 includes a type or identifier 615 and a value 620. Each graphical representation 610 is associated with one or more parameters affected the graphical display of the representation on the panel 605 to indicate a degree of relevance and/or urgency associated with the type 615 and value 620 of information displayed. For example, parameters of the graphical representation 610 can include size, shape, color, shading, etc. A degree of size, color, and/or shading, a type of shape, etc., can be used to indicate a relative degree of importance of the displayed information to a particular patient and/or user, for example.

As shown, for example, in FIG. 6, the panel 605 of the multi-resolution information display 600 provides vital signs and/or laboratory test results for a patient. The vitals panel 605 provides a visual indicator 610 of one or more vital signs and/or lab test results for the patient. For example, indicators 610 can include blood pressure (e.g., systolic and diastolic blood pressure), pulse rate, respiratory rate, temperature, etc. Each indicator 610 includes a type 615 and a value 620. For example, the diastolic blood pressure indicator 610 includes a type 615 (e.g., blood pressure) and a value 620 (e.g., 130, or a combined 200 over 130 for systolic and diastolic blood pressure together). Each indicator 610 has a certain color and/or a certain size, for example, to indicate an importance of the constituent information from the indicator 610. For example, the systolic and diastolic blood pressure indicators 610 are the largest sized indicators 610 in the panel 605, visually indicating to a user the relative importance of the blood pressure reading over the other results. Pulse and respiratory rates would follow as next in importance, etc. As another example, systolic and diastolic blood pressures 610 are colored red, pulse rate and respiratory rate are colored orange, and temperature is colored green. The color can be used to indicate a degree of severity or importance of the constituent value. For example, the blood pressures, colored red, would carry the most importance, the pulse and respiratory rates, colored orange, would be next in importance, etc. Thus, indicator size and/or color can be used together and/or separately to provide the user with an immediate visual indication of a priority to be placed on investigation of patient vitals and lab results. In certain embodiments, selection of an indicator 610 retrieves data, results, and/or document(s) used to generate the information for the indicator 610.

As shown, for example, in FIG. 6, positioning a cursor and/or otherwise selecting an indicator 610 (e.g., by mouse over or mouse click) provides a thumbnail view 625 of data such as graphical trend data, associated with that indicator 610. In the example of FIG. 6, a thumbnail 625 of diastolic blood pressure readings over time for the patient is displayed adjacent to the diastolic blood pressure indicator 610. In an alternative embodiment, the thumbnail view 625 can replace the particular indicator 610 and/or be overlaid at least partially on top of the corresponding indicator 610, for example. The thumbnail view 625 can provide a graph/chart representation of information and/or an alphanumeric reporting of the data, for example.

Selecting the thumbnail 625 (e.g., by mouse click, mouse over, and/or other cursor selection) provides a larger view 630 of the trend information, for example. As shown in FIG. 6, for example, a full view 630 of the trend information underlying the diastolic blood pressure indicator 610 provides a graph 635 of the data points and a chart 640 listing the values of the data points, for example. The full view 630 can be provided as part of the panel 605 and/or in a separate display overlaid on and/or adjacent to the panel 605, for example. For example, the full view 630 can be provided as another widget or display on a user interface separate from the panel 605. In certain embodiments, a user can add, remove, and/or modify data in the view 630. For example, a user can add an additional data point to the view 630 to generate a query and/or comparison of the new data point to one or more existing values. A comparison can include a re-evaluation of the trend of values, for example.

Selecting (e.g., via mouse over, mouse click, and/or other cursor action) a particular data point 645 on the view 630 provides a view of the original document 650 from which the data point 645 was obtained, for example. A user can view and/or modify information in the document 650 via the view, for example.

Figure 7:
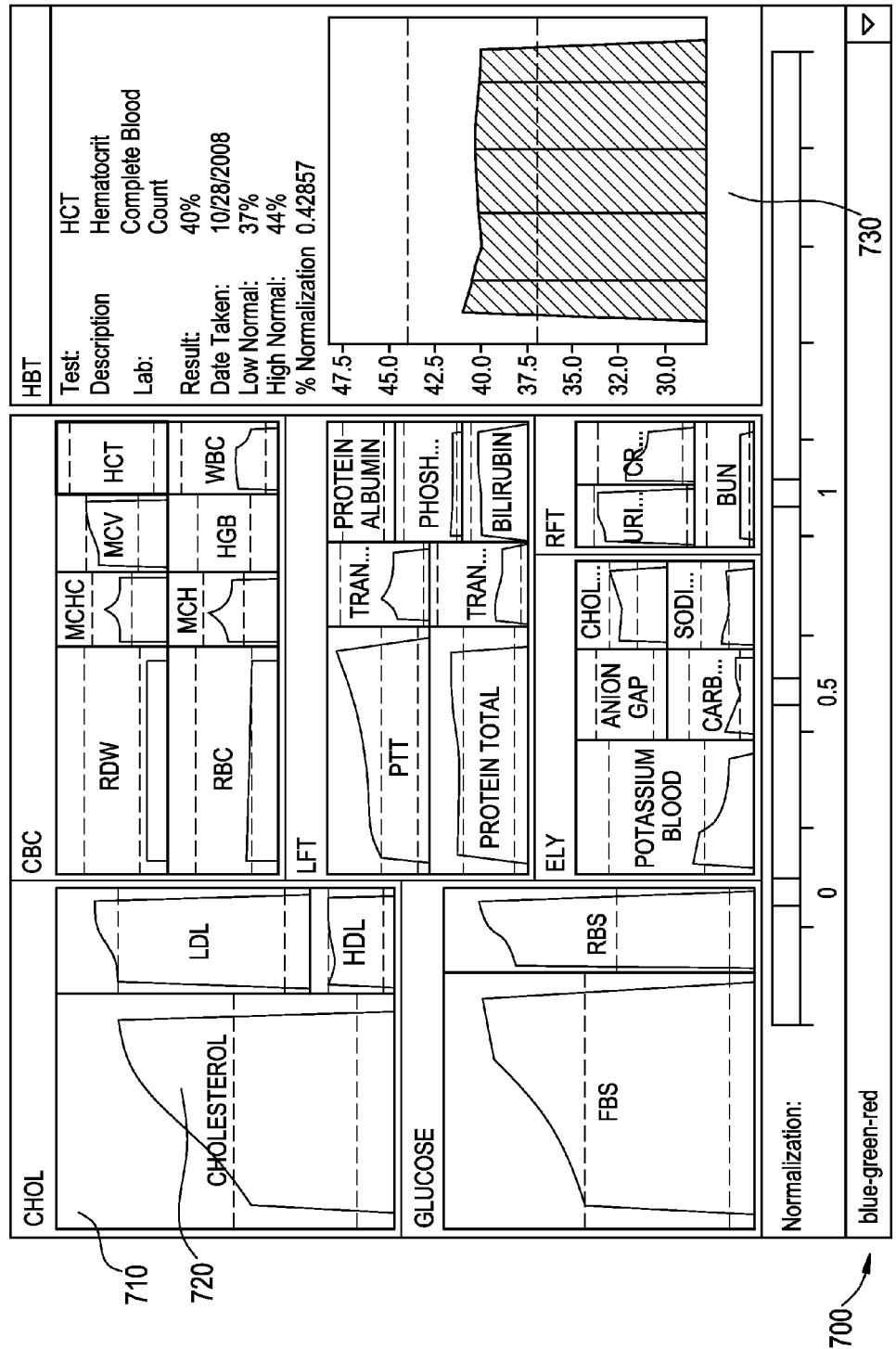
FIG. 7 illustrates a treemap visualization view of clinical results in accordance with certain embodiments of the present invention.

FIG. 7 illustrates a treemap visualization view 700 of clinical results in accordance with certain embodiments of the present invention. Prior systems allow clinicians to view lab results in a tabular form, and clinicians must evaluate for themselves where these values lie with respect to normal ranges. Rather than parsing through all this information to decide which lab results are of interest to them, a treemap, such as the treemap 700 shown in FIG. 7, allows clinicians to analyze a collection of lab results holistically as well as highlight particular tests that have yielded abnormal results. The treemap 700 breaks down into two dimensions: size and color. The size of each cell 710 is determined by which clinical level the cell falls in: normal, warning or panic, for example. Ranges used to determine a clinical level are predetermined and can be included in laboratory datasets. The color of each cell is controlled by where the value of the cell lies with respect to a normal range for values of that type. If a cell's value is in the normal range, it is colored a shade of green, which is determined by the value's position within the normal range. For example, if the value is right in the middle of the normal range, the cell is bright green as opposed to a value on the edge of the normal threshold, which will be a darker shade of green. The same applies to the abnormal ranges. If the value is just beyond the normal range, the shade of the cell is dark red, but, as the value moves farther and farther from the normal range, the cell becomes brighter red.

Therefore, if a lab result is out of range, it is colored red/blue and is larger than the green cells. The red and blue colors indicate whether the values are higher (red) or lower (blue) than the normal range (green), for example.

In addition to these two dimensions of size and color, a background of a cell can depict a trend 720 of the last few recorded values for that lab test. This provides more context indicating whether the lab result is gradually moving out of range or if there was an event that caused a huge spike in the result. It also shows high and low thresholds so that a user can see which direction the latest result is headed with respect to the normal range.

When a user positions a cursor (e.g., mouses over) any of these cells, a side panel 730 is populated with more specific lab data as well as another graph that has range values on its axis. With this type of visualization, doctors can glance at a collection of lab results and become aware of which lab tests are out of range and by how much those test results are out of range. Clinicians can then hopefully use these immediate clues to formulate a conclusion in a quicker manner than if they had viewed the results in a table.

Figure 8:
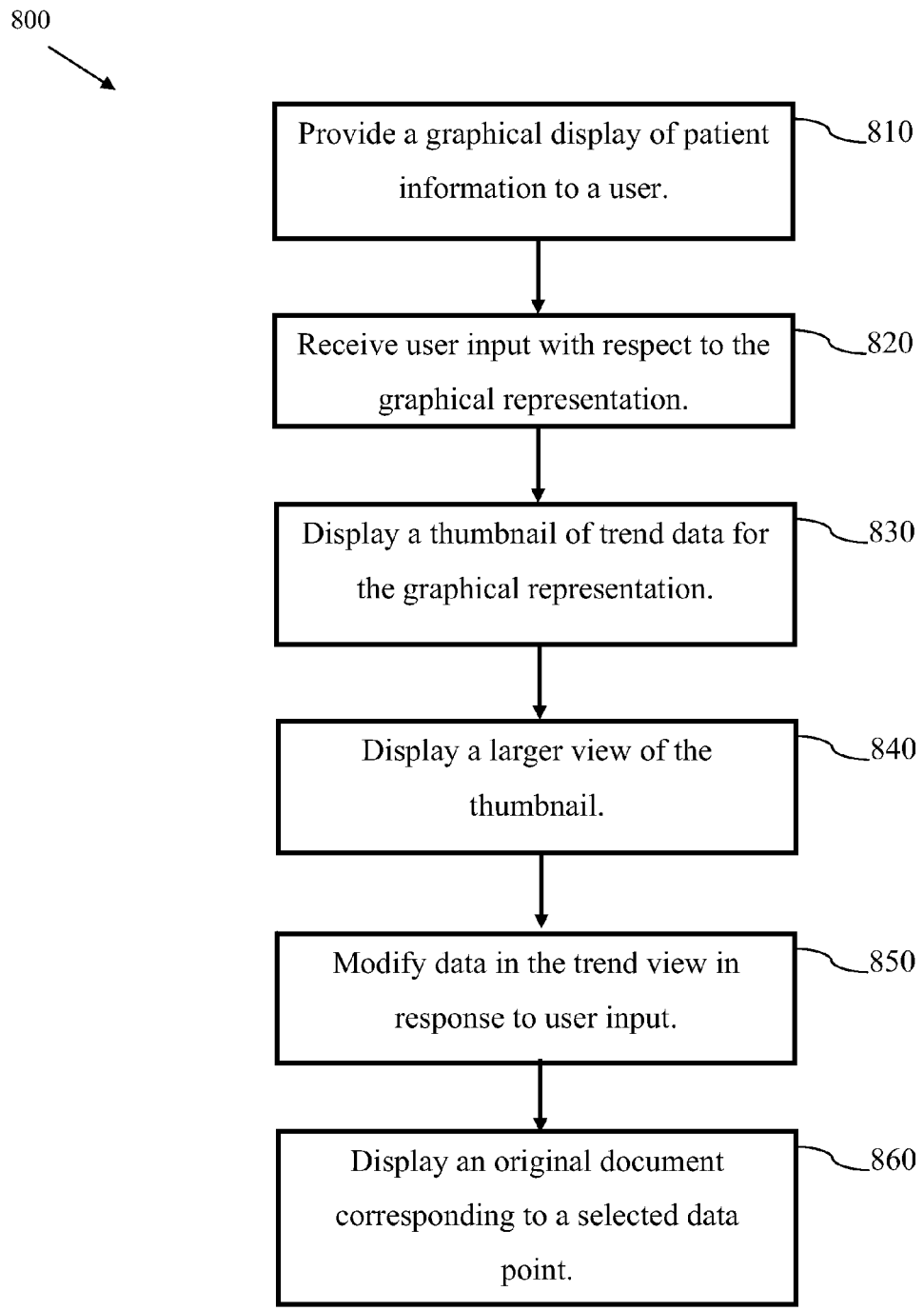
FIG. 8 shows a flow diagram for a method for access to health content via an adaptive, work-centered user interface and supporting architecture in accordance with certain embodiments of the present invention.

FIG. 8 shows a flow diagram for a method 800 for access to health content via an adaptive, work-centered user interface and supporting architecture in accordance with certain embodiments of the present invention.

At 810, a graphical display of patient information is provided to a user. For example, the graphical display includes a plurality of graphical representations related to patient clinical information. For example, each graphical representation can have one or more characteristics affected the graphical display of the representation to indicate a degree of relevance and/or urgency associated with the content of the information displayed. For example, characteristics of the graphical representation can include size, shape, color, shading, etc. A degree of size, color, and/or shading, a type of shape, etc., can be used to indicate a relative degree of importance of the displayed information to a particular patient and/or user, for example.

At 820, user input is received with respect to a graphical representation. For example, a user can position a cursor (e.g., via mouse over or mouse click) over a graphical representation.

At 830, in response to user input, a thumbnail view of trend data related to the graphical representation information is displayed for the user. For example, positioning a cursor and/or otherwise selecting a graphical representation (e.g., by mouse over or mouse click) provides a thumbnail view of data such as graphical trend data, associated with that indicator. As an example, mousing over a graphical representation of a blood pressure reading provides a thumbnail view of historical trend data related to the blood pressure reading. The thumbnail view can provide a graph/chart representation of information and/or an alphanumeric reporting of the data, for example.

At 840, in response to user input, a larger view of the trend information is displayed for the user. For example, selecting the thumbnail image (e.g., by mouse click, mouse over, and/or other cursor selection) provides a larger view of the trend information. That is, a larger and more interactive view of the historical trend data including, for example, a graph based view and an alphanumeric chart view of the data is provided to the user. For example, a full view of historical blood pressure data is provided the trend information underlying the graphical representation of blood pressure information, including a graph of the data points and a chart listing the values of the data points, for example.

At 850, a user can add, remove, and/or modify data in the trend view. For example, a user can add an additional data point to the view to generate a query and/or comparison of the new data point to one or more existing values. A comparison can include a re-evaluation of the trend of values, for example.

At 860, selecting (e.g., via mouse over, mouse click, and/or other cursor action) a particular data point on the trend view provides a view of the original document from which the data point was obtained. For example, selection of a historical blood pressure reading from the trend graph retrieves and displays a patient examination report from which the blood pressure reading was obtained. A user can view and/or modify information in the document via the view, for example.

One or more of the steps of the method 800 may be implemented alone or in combination in hardware, firmware, and/or as a set of instructions in software, for example. Certain examples may be provided as a set of instructions residing on a computer-readable medium, such as a memory, hard disk, DVD, or CD, for execution on a general purpose computer or other processing device.

Certain examples may omit one or more of these steps and/or perform the steps in a different order than the order listed. For example, some steps may not be performed in certain examples. As a further example, certain steps may be performed in a different temporal order, including simultaneously, than listed above.

Thus, certain embodiments provide a plurality of benefits including a single point of access, cross-modality data access, XDS compliance, push and pull capability, consensus building, transparency, knowledge management enhanced by use, cross platform (Web, mobile, etc.) accessibility, and a system level view of a user's information space, for example.

Certain embodiments provide an architecture and framework for a variety of clinical applications. The framework can include front-end components including but not limited to a Graphical User Interface (GUI) and can be a thin client and/or thick client system to varying degree, which some or all applications and processing running on a client workstation, on a server, and/or running partially on a client workstation and partially on a server, for example.

The example user interface systems and methods described herein can be used in conjunction with one or more clinical information systems, such as a hospital information system ("HIS"), a radiology information system ("RIS"), a picture archiving and communication system ("PACS"), a cardiovascular information system ("CVIS"), a library information system ("LIS"), an enterprise clinical information system ("ECIS"), an electronic medical record system ("EMR"), a laboratory results/order system, etc. Such systems can be implemented in software, hardware, and/or firmware, for example. In certain implementations, one or more of the systems can be implemented remotely via a thin client and/or downloadable software solution. Furthermore, one or more components can be combined and/or implemented together.

Figure 9:
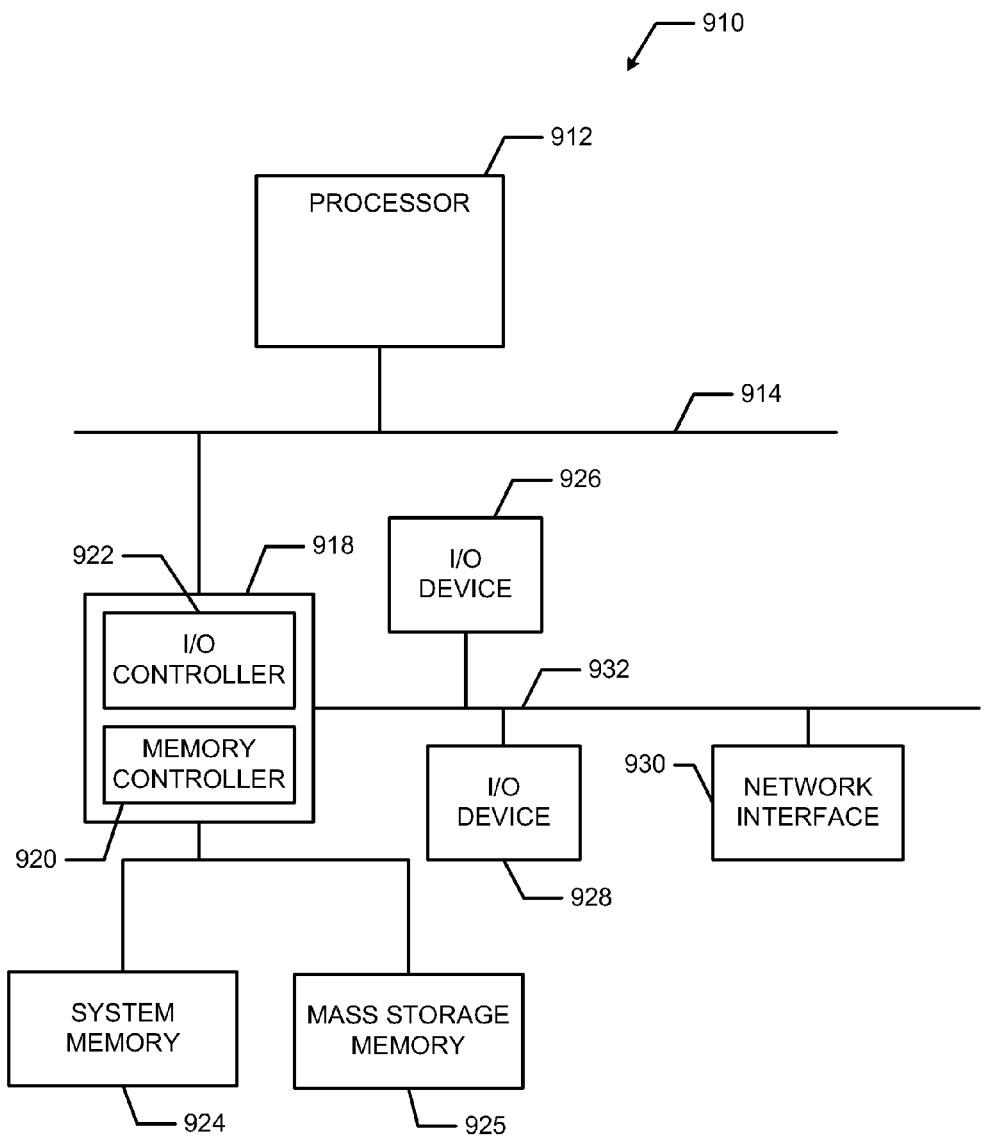
FIG. 9 shows a block diagram of an example processor system that may be used to implement systems and methods described herein.

FIG. 9 is a block diagram of an example processor system 910 that may be used to implement systems and methods described herein. As shown in FIG. 9, the processor system 910 includes a processor 912 that is coupled to an interconnection bus 914. The processor 912 may be any suitable processor, processing unit, or microprocessor, for example. Although not shown in FIG. 9, the system 910 may be a multi-processor system and, thus, may include one or more additional processors that are identical or similar to the processor 912 and that are communicatively coupled to the interconnection bus 914.

The processor 912 of FIG. 9 is coupled to a chipset 918, which includes a memory controller 920 and an input/output ("I/O") controller 922. As is well known, a chipset typically provides I/O and memory management functions as well as a plurality of general purpose and/or special purpose registers, timers, etc. that are accessible or used by one or more processors coupled to the chipset 918. The memory controller 920 performs functions that enable the processor 912 (or processors if there are multiple processors) to access a system memory 924 and a mass storage memory 925.

The system memory 924 may include any desired type of volatile and/or nonvolatile memory such as, for example, static random access memory (SRAM), dynamic random access memory (DRAM), flash memory, read-only memory (ROM), etc. The mass storage memory 925 may include any desired type of mass storage device including hard disk drives, optical drives, tape storage devices, etc.

The I/O controller 922 performs functions that enable the processor 912 to communicate with peripheral input/output ("I/O") devices 926 and 928 and a network interface 930 via an I/O bus 932. The I/O devices 926 and 928 may be any desired type of I/O device such as, for example, a keyboard, a video display or monitor, a mouse, etc. The network interface 930 may be, for example, an Ethernet device, an asynchronous transfer mode ("ATM") device, an 802.11 device, a DSL modem, a cable modem, a cellular modem, etc. that enables the processor system 910 to communicate with another processor system.

While the memory controller 920 and the I/O controller 822 are depicted in FIG. 9 as separate blocks within the chipset 918, the functions performed by these blocks may be integrated within a single semiconductor circuit or may be implemented using two or more separate integrated circuits.

Thus, certain embodiments provide for access by an end user to information across enterprise systems. Certain embodiments provide a technical effect of a search-driven, role-based, workflow-based, and/or disease-based interface that allows the end user to access, input, and search medical information seamlessly across a healthcare network. Certain embodiments offer adaptive user interface capabilities through a work-centered interface tailored to individual needs and responsive to changes in a work domain. Certain embodiments introduce an adaptive, work-centered user interface technology software architecture, which uses an ontology modeling approach to characterize a work domain in terms of "work-centered" activities as well as computation mechanisms to achieve an implementation that supports those activities and provides adaptive interaction, both user directed and automated, in work-centered characterization and presentation mechanisms of the user interface to enterprise-level applications.

Certain embodiments provide an adaptive user interface that leverages semantic technology to model domain concepts, user roles and tasks, and information relationships, for example. Semantic models enable applications to find, organize and present information to users more effectively based on contextual information about the user and task. Applications can be composed from libraries of information widgets to display multi-content and multi-media information. In addition, the framework enables users to tailor the layout of the widgets and interact with the underlying data.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A multi-level information display system graphically representing clinical information for a user, said system comprising:

a display screen including a single unified user interface to provide clinical content to a user at a plurality of levels of resolution based on user interaction with the interface and accept user input with respect to clinical content to trigger access to each of the plurality of levels of granularity for the clinical content via the single unified user interface; and a processor to provide a plurality of levels of resolution for the clinical content within the single unified user interface, the plurality of levels of resolution comprising:

a graphical summary representation of a patient-related clinical data value, the graphical summary representation having one or more visible characteristics indicating an importance of the patient-related clinical data value, the graphical summary representation displayed to the user via a first panel occupying a portion of the user interface triggered by selection of a patient via the user interface;

a thumbnail trend view providing a graph of data elements used to provide the patient-related clinical data value shown in the graphical summary representation, the thumbnail trend view triggered for display via the user interface upon a positioning of a cursor over the graphical summary representation, the thumbnail trend view to be displayed in a second panel positioned in or with the first panel showing the graphical summary representation;

a full trend view providing an enlarged graph of data elements used to provide the patient-related clinical data value shown in the graphical summary representation and the thumbnail trend view, the full trend view triggered for display via the user interface upon a selection of the thumbnail trend view, the full trend view to be displayed in a third panel positioned at least adjacent to the second panel showing the thumbnail trend view and the first panel showing the graphical summary representation, wherein the user interface facilitates dragging and dropping of a data element onto the graph of the full trend view to compare values of the data elements; and an originating data view retrieving and displaying, via the user interface in a fourth panel, a source document corresponding to at least one data element on the graph shown in the thumbnail trend view, the originating data view triggered for display via the user interface upon a selection of the at least one data element on the graph shown in the thumbnail trend view.

2. The system of claim 1, wherein the user interface facilitates modification of at least one of the graph of data points in the thumbnail trend view and the source document in the originating data view by a user.

3. The system of claim 1, wherein the thumbnail trend view is displayed adjacent to and commensurate in size with the graphical summary representation.

4. The system of claim 1, wherein the originating data view is at least partially overlaid on the graphical summary representation.

5. The system of claim 1, wherein the originating data view provides the source document complete with data context.

6. The system of claim 1, wherein the one or more visible characteristics of the graphical summary representation include size and color, wherein the size and color indicate a degree of importance of the clinical data value.

7. The system of claim 1, wherein the graphical summary representation, the thumbnail trend view, and the originating data view are provided in a widget accessible via the user interface.

8. A method for graphical, multi-level information display of patient clinical information to a user, said method comprising:

generating, using a processor via a display screen, a user interface providing clinical content to a user at a plurality of levels of resolution based on user interaction with the interface and accepting user input with respect to clinical content to trigger access to each of the plurality of levels of resolution for the clinical content via the single unified user interface;

providing, using the processor, a graphical summary representation of a patient-related clinical data value as a first level of resolution, the graphical summary representation having one or more visible characteristics indicating an importance of the patient-related clinical data value, the graphical summary representation displayed to the user via a first panel occupying a portion of the user interface triggered by selection of a patient via the user interface;

providing, using the processor, a thumbnail trend view including a graph of data elements used to provide the patient-related clinical data value shown in the graphical summary representation as a second level of resolution, the thumbnail trend view triggered for display via the user interface upon a positioning of a cursor over the graphical summary representation, the thumbnail trend view to be displayed in a second panel positioned in or with the first panel showing the graphical summary representation;

providing, using the processor, a full trend view including an enlarged graph of data elements used to provide the patient-related clinical data value shown in the graphical summary representation and the thumbnail trend view as a third level of resolution, the full trend view triggered for display via the user interface upon a selection of the thumbnail trend view, the full trend view to be displayed in a third panel positioned at least adjacent to the second panel showing the thumbnail trend view and the graphical summary representation, wherein the user interface facilitates dragging and dropping of a data element onto the graph of the full trend view to compare values of the data elements; and providing, using the processor, an originating data view retrieving and displaying, via the user interface in a fourth panel, a source document corresponding to at least one data element on the graph shown in the thumbnail trend view as a fourth level of resolution, the originating data view triggered for display via the user interface upon a selection of the at least one data element on the graph shown in the thumbnail trend view.

9. The method of claim 8, further comprising facilitating modification of at least one of the graph of data points in the thumbnail trend view and the source document in the originating data view by a user via the user interface.

10. The method of claim 8, wherein the thumbnail trend view is displayed adjacent to and commensurate in size with the graphical summary representation.

11. The method of claim 8, wherein the originating data view is at least partially overlaid on the graphical summary representation.

12. The method of claim 8, wherein the originating data view provides the source document complete with data context.

13. The method of claim 8, wherein the one or more visible characteristics of the graphical summary representation include size and color, wherein the size and color indicate a degree of importance of the clinical data value.

14. The method of claim 8, wherein the graphical summary representation, the thumbnail trend view, and the originating data view are provided in a widget accessible via the user interface.

15. A non-transitory machine readable storage device having a set of instructions for execution on a computing device, the set of instructions, when executed, generating a multi-level information display system graphically representing clinical information for a user, the set of instructions comprising:

a single unified user interface to provide clinical content to a user at a plurality of levels of resolution based on user interaction with the interface and accept user input with respect to clinical content to trigger access to each of the plurality of levels of granularity for the clinical content via the single unified user interface; and a processor to provide a plurality of levels of resolution for the clinical content within the single unified user interface, the plurality of levels of resolution comprising:

a graphical summary representation of a patient-related clinical data value, the graphical summary representation having one or more visible characteristics indicating an importance of the patient-related clinical data value, the graphical summary representation displayed to the user via a first panel occupying a portion of the user interface triggered by selection of a patient via the user interface;

a thumbnail trend view providing a graph of data elements used to provide the patient-related clinical data value shown in the graphical summary representation, the thumbnail trend view triggered for display via the user interface upon a positioning of a cursor over the graphical summary representation, the thumbnail trend view to be displayed in a second panel positioned in or with the first panel showing the graphical summary representation;

a full trend view providing an enlarged graph of data elements used to provide the patient-related clinical data value shown in the graphical summary representation and the thumbnail trend view, the full trend view triggered for display via the user interface upon a selection of the thumbnail trend view, the full trend view to be displayed in a third panel positioned at least adjacent to the second panel showing the thumbnail trend view and the first panel showing the graphical summary representation, wherein the user interface facilitates dragging and dropping of a data element onto the graph of the full trend view to compare values of the data elements; and an originating data view retrieving and displaying, via the user interface in a fourth panel, a source document corresponding to at least one data element on the graph shown in the thumbnail trend view, the originating data view triggered for display via the user interface upon a selection of the at least one data element on the graph shown in the thumbnail trend view.

\* \* \* \* \*